United States Patent
Pratt et al.

(10) Patent No.: US 10,994,062 B2
(45) Date of Patent: May 4, 2021

(54) NEGATIVE-PRESSURE THERAPY WITH ADJUSTABLE INSTILLATION PUMP CHAMBER

(71) Applicant: KCI Licensing, Inc., San Antonio, TX (US)

(72) Inventors: Benjamin Andrew Pratt, Poole (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 324 days.

(21) Appl. No.: 16/036,357

(22) Filed: Jul. 16, 2018

(65) Prior Publication Data

US 2019/0022289 A1     Jan. 24, 2019

Related U.S. Application Data

(60) Provisional application No. 62/533,729, filed on Jul. 18, 2017.

(51) Int. Cl.
| | | |
|---|---|---|
| A61M 1/00 | (2006.01) | |
| A61M 27/00 | (2006.01) | |
| A61M 3/02 | (2006.01) | |

(52) U.S. Cl.
CPC ........ *A61M 1/0088* (2013.01); *A61M 1/0058* (2013.01); *A61M 1/0084* (2013.01);
(Continued)

(58) Field of Classification Search
CPC .............. A61M 1/0058; A61M 1/0088; A61M 3/0208; A61M 3/022; A61M 1/0084; A61M 3/0283; A61M 27/00; A61M 1/0049
See application file for complete search history.

(56) References Cited

U.S. PATENT DOCUMENTS 1,355,846 A   10/1920  Rannells
2,547,758 A   4/1951   Keeling
(Continued)

FOREIGN PATENT DOCUMENTS

AU   550575 B2   3/1986
AU   745271 B2   3/2002
(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Tatyana Zalukaeva
*Assistant Examiner* — Jessica R Arble

(57) ABSTRACT

Systems, apparatuses, and methods for instilling fluid to a tissue site in a negative-pressure therapy environment are described. Illustrative embodiments may include a pneumatically-actuated installation pump that can draw a solution from a solution source during a negative-pressure interval, and instill the solution to a dressing during a venting interval. A pneumatic actuator may be mechanically coupled to a disposable distribution system that can provide a fluid path between the solution source and a distribution component. A bacterial filter may be disposed in the fluid path between the actuator and the distribution component to prevent contamination of the actuator during operation. The distribution system may be separated from the actuator and disposed of after operation, and the actuator may be re-used.

20 Claims, 9 Drawing Sheets

(52) U.S. Cl.
CPC .......... *A61M 3/022* (2014.02); *A61M 3/0208* (2014.02); *A61M 3/0283* (2013.01); *A61M 27/00* (2013.01); *A61M 1/0049* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,024,720 A * | 2/2000 | Chandler | A61M 1/0058 604/35 |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2009/0030402 A1* | 1/2009 | Adahan | A61M 1/0092 604/540 |
| 2014/0163491 A1 | 6/2014 | Schuessler et al. | |
| 2014/0188061 A1* | 7/2014 | Locke | A61M 1/0009 604/321 |
| 2015/0080788 A1 | 3/2015 | Blott et al. | |
| 2015/0094674 A1* | 4/2015 | Pratt | A61M 1/0035 604/318 |
| 2016/0015872 A1 | 1/2016 | Luckemeyer et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |

(56) References Cited

FOREIGN PATENT DOCUMENTS

| | | | |
|---|---|---|---|
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | 2014043225 A2 | 3/2014 | |
| WO | 2016040671 A1 | 3/2016 | |
| WO | WO-2016040671 A1 * | 3/2016 | ....... A61F 13/00042 |
| WO | 2016126560 A1 | 8/2016 | |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirugi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

(56) References Cited

OTHER PUBLICATIONS

International Search Report and Written Opinion for Corresponding Application No. PCT/US2018/042261, dated Jan. 29, 2019.

\* cited by examiner

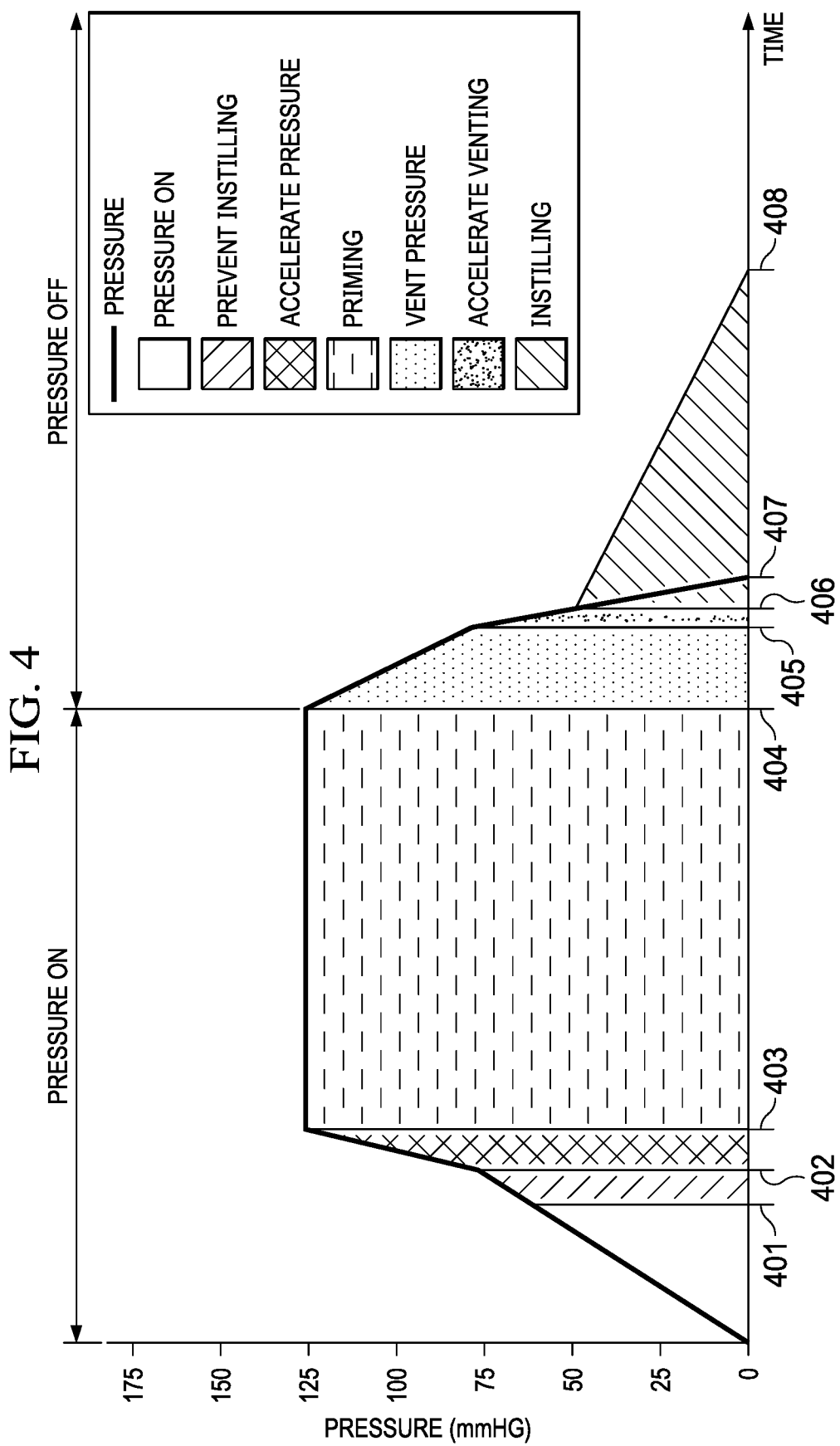

NEGATIVE-PRESSURE THERAPY WITH ADJUSTABLE INSTILLATION PUMP CHAMBER

RELATED APPLICATION

This application claims the benefit, under 35 USC 119(e), of the filing of U.S. Provisional Patent Application No. 62/533,729, entitled "NEGATIVE-PRESSURE THERAPY WITH ADJUSTABLE INSTILLATION PUMP CHAMBER," filed Jul. 18, 2017, which is incorporated herein by reference for all purposes.

TECHNICAL FIELD

The invention set forth in the appended claims relates generally to tissue treatment systems and more particularly, but without limitation, to apparatuses and methods for providing negative-pressure therapy with instillation of topical treatment solutions.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and instillation therapy are widely known, improvements to therapy systems, components, and processes may benefit healthcare providers and patients.

BRIEF SUMMARY

New and useful systems, apparatuses, and methods for instilling fluid to a tissue site in a negative-pressure therapy environment are set forth in the appended claims. Illustrative embodiments are also provided to enable a person skilled in the art to make and use the claimed subject matter. Some embodiments are illustrative of an apparatus or system for delivering therapeutic solution of fluids to a tissue site, which can be used in conjunction with negative-pressure therapy. For example, an apparatus may include a pneumatically-actuated instillation pump that can draw a solution from a solution source during a negative-pressure interval, and instill the solution to a dressing during a venting interval.

In some embodiments, for example, a pneumatic actuator may be mechanically coupled to a disposable distribution system. The distribution system may generally comprise a dosing chamber, and one or more fluid conductors that can provide a fluid path between the dosing chamber and a solution source, and between the dosing chamber and a distribution component, such as a dressing or dressing interface. One or more fluid conductors may also provide a fluid path between the actuator and a distribution component. A bacterial filter may be disposed in the fluid path between the actuator and the distribution component to prevent contamination of the actuator during operation. The distribution system may be separated from the actuator and disposed of after operation, and the actuator may be re-used.

More generally, some embodiments of an apparatus for managing fluid in a system for negative-pressure therapy may include a dosing chamber having a dosing inlet and a dosing outlet. A first check valve may be fluidly coupled to the dosing inlet, and a second check valve may be fluidly coupled to the dosing outlet. A first fluid conductor can be fluidly coupled to the second check valve and a fluid port. A second fluid conductor can be fluidly coupled to the fluid port and a fluid fitting that can be configured to be coupled to a negative-pressure source. A filter can be fluidly coupled to the second fluid conductor between the fluid port and the fluid fitting to prevent contamination of other components in the system.

In more specific examples, the fluid port may comprise a dressing pad configured to provide fluid to the tissue site. In some embodiments, the dressing pad can be configured to fluidly couple the first conductor to the second conductor. The apparatus may further comprise a control valve fluidly coupled to the first fluid conductor. The apparatus may further include a liquid coupling, such as a spike connector, configured to couple the dosing chamber to a solution source. In some embodiments, the apparatus may additionally or alternatively include a solution source.

The apparatus may additionally include an instillation actuator in some embodiments. Such an instillation actuator may be fluidly coupled to the fluid fitting and mechanically coupled to the dosing chamber. The fluid coupling and the mechanical coupling are both preferably temporary couplings, adapted to allow the instillation actuator to be routinely coupled to and removed from the fluid fitting and the dosing chamber without compromising the integrity of any components. The instillation actuator may be configured to expand and contract the dosing chamber. For example, in some embodiments, the instillation actuator may comprise a piston chamber and a piston operably engaged to the dosing chamber. Pressure changes in the piston chamber can actuate the piston to expand and contract the dosing chamber. In some embodiments, expansion of the dosing chamber can draw solution into the dosing chamber, and contraction of the dosing chamber can expel the solution from the dosing chamber.

The instillation actuator also may be configured to open and close the priming chamber. For example, in some embodiments, the instillation actuator may comprise a piston chamber and a piston operably engaged to the priming chamber. Pressure changes in the piston chamber can actuate the piston to open and close the priming chamber. In some embodiments, opening of the priming chamber can draw solution into the priming chamber to provide the solution to the dosing chamber, and closing the primary chamber can allow the dosing chamber to expel the solution from the dosing chamber.

In some example embodiments, the apparatus may further comprise a negative-pressure source fluidly coupled to the fluid fitting and the fluid port. The negative-pressure source may provide negative-pressure intervals when activated and venting intervals when deactivated. In operation, the instillation actuator can expand the dosing chamber during a negative-pressure interval to draw a dose of solution from a solution source, and can contract the dosing chamber during a venting interval to expel the dose of solution from the dosing chamber to a dressing or other distribution component.

Alternatively, other example embodiments may include a system for providing negative-pressure and instillation therapy. The system may include a negative-pressure source and a controller electrically coupled to the negative-pressure source and configured to turn on the negative-pressure source during a negative-pressure interval and turning off the negative-pressure source during a venting interval. The system may further include an actuator and a distribution system. The actuator may comprise a dosing piston and a priming piston configured to be coupled to the negative-pressure source. The distribution system may comprise a priming chamber, a dosing chamber, a fluid port, and a fluid fitting in some embodiments. The priming chamber may be fluidly coupled to the dosing chamber. The fluid port may be configured to be fluidly coupled to the dosing chamber and to the fluid fitting configured to be coupled to the negative-pressure source. The actuator is preferably configured to expand the dosing chamber during the negative-pressure interval and contract the dosing chamber during the venting interval. In some embodiments, the actuator may also be configured to open the priming chamber during the negative-pressure interval to provide solution to the dosing chamber, and to close the priming chamber during the venting interval.

In other embodiments of an apparatus for managing fluid in a system for managing fluids in a system for providing negative-pressure therapy to a tissue site, the apparatus may comprise a dosing valve having a dosing chamber including a dosing inlet and a dosing outlet, and a first check valve fluidly coupled to the dosing inlet and configured to be coupled by a first fluid conductor to a source of liquids. Such apparatus may further comprise a priming valve having a priming chamber fluidly coupled between the first check valve and the fluid inlet, and a second check valve fluidly coupled to the dosing outlet. The apparatus may further comprise a control valve fluidly coupled to the second check valve by a second fluid conductor, and a fluid port fluidly coupled to the control valve by a third fluid conductor. The apparatus also may comprise a fluid fitting fluidly coupled to the fluid port by a fourth fluid conductor and configured to be coupled to a negative-pressure source. In some embodiments, the dosing valve may further comprise a first working chamber fluidly coupled to the fluid fitting and a first piston operably engaged to the dosing chamber and configured to be actuated by pressure changes in the first piston chamber to expand and contract the dosing chamber. In some embodiments, the priming valve may further comprise a second working chamber fluidly coupled to the fluid fitting and a second piston operably engaged to the priming chamber to be actuated by pressure changes in the second piston chamber to open and close the priming chamber.

A method for managing fluid in a therapy system may include fluidly coupling an apparatus or system as described to a dressing, which can be applied to a tissue site. Negative pressure may be applied to the tissue site for a first interval, in which instillation solution may be drawn into the dosing chamber. Negative pressure may be vented from the tissue site for a second interval, in which instillation solution can be delivered from the apparatus to the tissue site.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 4 is a graph illustrating additional details of the distribution system that may be associated with some embodiments of the therapy system of FIG. 1, including some embodiments of an instillation pump and an example embodiment of a valve activation sequence during a negative-pressure interval and a venting interval;

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

Figure 1:
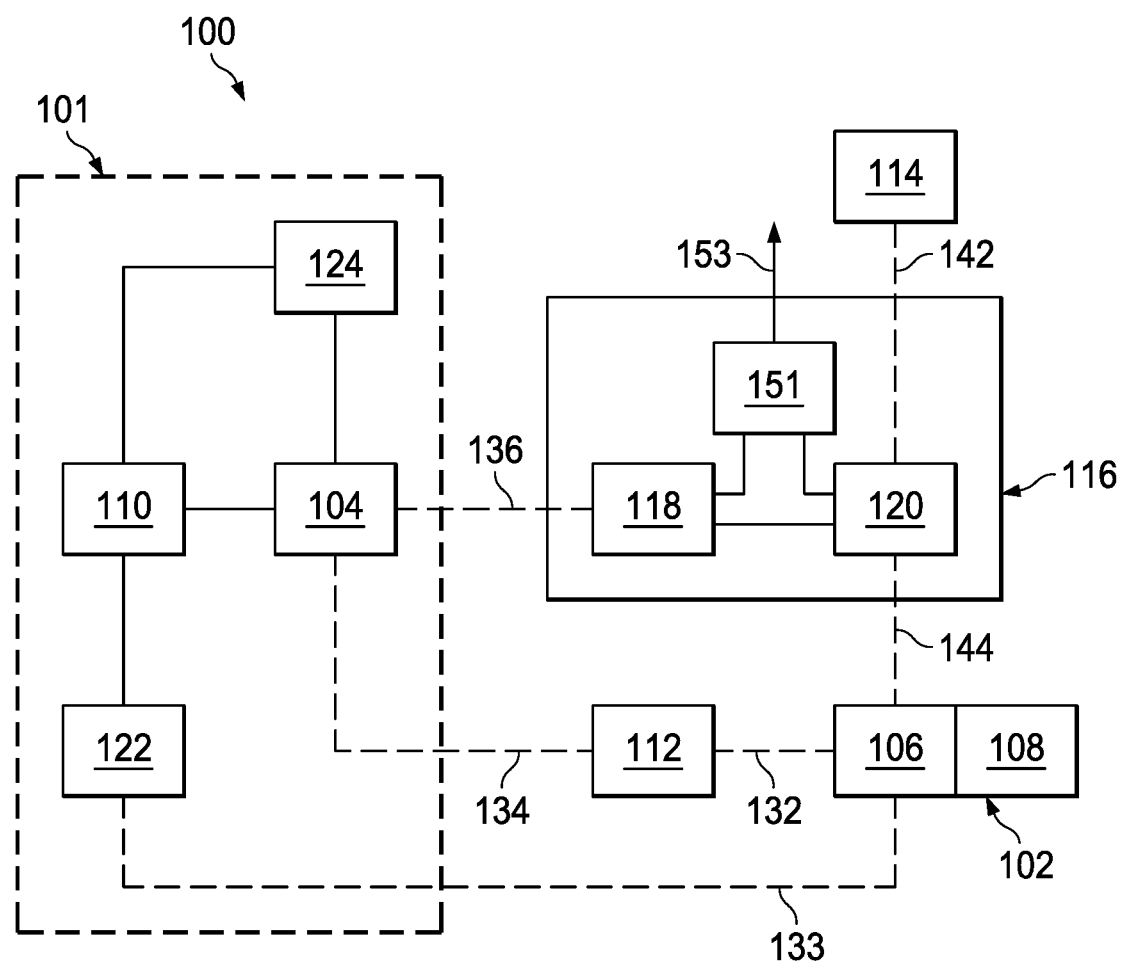
FIG. 1 is a functional block diagram of a first example embodiment of a therapy system that can provide negative-pressure and instillation in accordance with this specification.

FIG. 1 is a simplified functional block diagram of an example embodiment of a therapy system 100 that can provide negative-pressure therapy with instillation of topical treatment solutions to a tissue site in accordance with this specification. The therapy system 100 may include a negative-pressure supply, and may include or be configured to be coupled to a distribution component, such as a dressing. In general, a distribution component may refer to any complementary or ancillary component configured to be fluidly coupled to a negative-pressure supply between a negative-pressure supply and a tissue site. A distribution component is preferably detachable, and may be disposable, reusable, or recyclable. For example, a dressing 102 is illustrative of a distribution component fluidly coupled to a negative-pressure source 104 in FIG. 1. A dressing may include a cover, a tissue interface, or both in some embodiments. The dressing 102, for example, may include a cover 106 and a tissue interface 108. A controller, such as a controller 110, may also be coupled to the negative-pressure source 104.

In some embodiments, another distribution component, such as a dressing interface, may facilitate coupling the negative-pressure source 104 to the dressing 102. For example, a dressing interface may be a T.R.A.C.® Pad or Sensa T.R.A.C.® Pad available from KCI of San Antonio, Tex. The therapy system 100 may optionally include a fluid container, such as a container 112, coupled to the dressing 102 and to the negative-pressure source 104 such as, for example, by fluid conductors 132 and 134, respectively.

The therapy system 100 may also include a source of instillation solution, such as a solution source 114. A distribution component may be fluidly coupled to a fluid path between a solution source and a tissue site in some embodiments. For example, an instillation pump 116 may be coupled to the solution source 114, as illustrated in the example embodiment of FIG. 1. In some embodiments, the instillation pump 116 may comprise an actuator, such as an instillation actuator 118, and a pump chamber, such as a dosing chamber 120. For example, the dosing chamber 120 may be fluidly coupled to the solution source 114 by a fluid conductor 142 and to the dressing 102 by a fluid conductor 144. The instillation actuator 118 may be coupled to the dosing chamber 120 in some embodiments. In FIG. 1, for example, the instillation actuator 118 may be mechanically coupled to the dosing chamber 120. The instillation actuator 118 may also be fluidly coupled to the negative-pressure source 104 such as, for example, by a fluid conductor 136. In some embodiments, the instillation actuator 118 may be directly coupled to the negative-pressure source 104, as illustrated in FIG. 1, but may be indirectly coupled to the negative-pressure source 104 through other distribution components in some embodiments. For example, in some embodiments, the instillation actuator 118 may be fluidly coupled to the negative-pressure source 104 through the dressing 102

Additionally, the therapy system 100 may include sensors to measure operating parameters and provide feedback signals to the controller 110 indicative of the operating parameters. As illustrated in FIG. 1, for example, the therapy system 100 may include a pressure sensor 122, an electric sensor 124, or both, coupled to the controller 110. The pressure sensor 122 may also be coupled or configured to be coupled to a distribution component and to the negative-pressure source 104.

Components may be fluidly coupled to each other to provide a distribution system for transferring fluids (i.e., liquid and/or gas). For example, a distribution system may include various combinations of fluid conductors and fittings to facilitate fluid coupling. A fluid conductor generally includes any structure with one or more lumina adapted to convey a fluid between two ends, such as a tube, pipe, hose, or conduit. Typically, a fluid conductor is an elongated, cylindrical structure with some flexibility, but the geometry and rigidity may vary. Some fluid conductors may be molded into or otherwise integrally combined with other components. A fitting can be used to mechanically and fluidly couple components to each other. For example, a fitting may comprise a projection and an aperture. The projection may be configured to be inserted into a fluid conductor so that the aperture aligns with a lumen of the fluid conductor. A valve is a type of fitting that can be used to control fluid flow. For example, a check valve can be used to substantially prevent return flow. A port is another example of a fitting. A port may also have a projection, which may be threaded, flared, tapered, barbed, or otherwise configured to provide a fluid seal when coupled to a component.

In some embodiments, components may also be coupled by virtue of physical proximity, being integral to a single structure, or being formed from the same piece of material. Coupling may also include mechanical, thermal, electrical, or chemical coupling (such as a chemical bond) in some contexts. For example, a tube may mechanically and fluidly couple the dressing 102 to the container 112 in some embodiments. In general, components of the therapy system 100 may be coupled directly or indirectly. For example, the negative-pressure source 104 may be directly coupled to the controller 110, and may be indirectly coupled to the dressing 102 through the container 112.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the tissue interface 108 may be a foam having pore sizes in a range of 400-600 microns. The tensile strength of the tissue interface 108 may also vary according to needs of a prescribed therapy. For example, the tensile strength of a foam may be increased for instillation of topical treatment solutions. In one non-limiting example, the tissue interface 108 may be an open-cell, reticulated polyurethane foam such as GranuFoam® dressing or VeraFlo® foam, both available from Kinetic Concepts, Inc. of San Antonio, Tex.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m^2 per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 108, for example. The controller 110 is also preferably configured to receive one or more input signals, such as a feedback signal, and programmed to modify one or more operating parameters based on the input signals.

Sensors, such as the pressure sensor 122 or the electric sensor 124, are generally known in the art as any apparatus operable to detect or measure a physical phenomenon or property, and generally provide a signal indicative of the phenomenon or property that is detected or measured. For example, the pressure sensor 122 and the electric sensor 124 may be configured to measure one or more operating parameters of the therapy system 100. In some embodiments, the pressure sensor 122 may be a transducer configured to measure pressure in a pneumatic pathway and convert the measurement to a signal indicative of the pressure measured. In some embodiments, for example, the pressure sensor 122 may be a piezoresistive strain gauge. The electric sensor 124 may optionally measure operating parameters of the negative-pressure source 104, such as the voltage or current, in some embodiments. Preferably, the signals from the pressure sensor 122 and the electric sensor 124 are suitable as an input signal to the controller 110, but some signal conditioning may be appropriate in some embodiments. For example, the signal may need to be filtered or amplified before it can be processed by the controller 110. Typically, the signal is an electrical signal, but may be represented in other forms, such as an optical signal.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The solution source 114 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In some embodiments, the system 100 may be configured to separate components for receiving, coupling, or transmitting fluids from those components configured as part of a control system that in some embodiments may be a standard or pre-existing device for providing and controlling the application of negative pressure. For example, the system 100 may comprise a negative pressure device such as negative pressure device 101 that may be a pre-existing device including the negative pressure source 104 along with the controller 110, the pressure sensor 122, and the electronic sensors 124 as described above in more detail. The negative pressure device 101 may further comprise other control and/or communication devices that may be associated with additional features of the controller 110. For example, the negative pressure device 101 may include a wireless transceiver (not shown) coupled to the controller 110 for communicating commands and data with other components of the system 100. The system 100 may include an instillation pump such as, for example, the instillation pump 116, the comprises a wireless transceiver 150 coupled to the instillation actuator 118 and the dosing chamber 120 described above that communicates with the wireless transceiver contained within the negative pressure device 101 as indicated by the arrow 151. In some embodiments of negative pressure system such as the system 100 may comprise separate modules that may be integrated including the negative pressure device 101, the container 112, the solution source 114, and the instillation pump 116 all of which may be fluidly coupled to the dressing 102.

In operation, the tissue interface 108 may be placed within, over, on, or otherwise proximate to a tissue site. The cover 106 may be placed over the tissue interface 108 and sealed to an attachment surface near the tissue site. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in container 112. In some embodiments, negative pressure may be applied intermittently or periodically, with intervals of negative pressure and intervals of venting or positive pressure.

During negative-pressure intervals, negative pressure can actuate the instillation actuator 118, which can operate the dosing chamber 120. For example, in some embodiments, the instillation actuator 118 can expand the dosing chamber 120 during a negative-pressure interval, lowering pressure in the dosing chamber 120 and drawing instillation solution into the dosing chamber 120 from the solution source 114 through a first check valve, which can substantially prevent return of the instillation solution from the dosing chamber 120 to the solution source 114. During a subsequent venting interval, the instillation actuator 118 can contract the dosing chamber 120, increasing the pressure in the dosing chamber 120 and expelling instillation solution from the dosing chamber 120 through a second check valve to the dressing 102. The second check valve can substantially prevent return of the instillation solution (as well as exudate) to the dosing chamber 120. The instillation solution may dwell at the tissue site for the duration of the venting interval, and then be removed from the tissue site and drawn into the container 112 during a subsequent negative-pressure interval. A filter can be disposed between the instillation actuator 118 and the dressing 102 to prevent contamination of the instillation actuator 118. For example, the filter may be a bacterial filter configured to remove bacteria from fluid flowing through the filter from the dressing 102.

Figure 2:
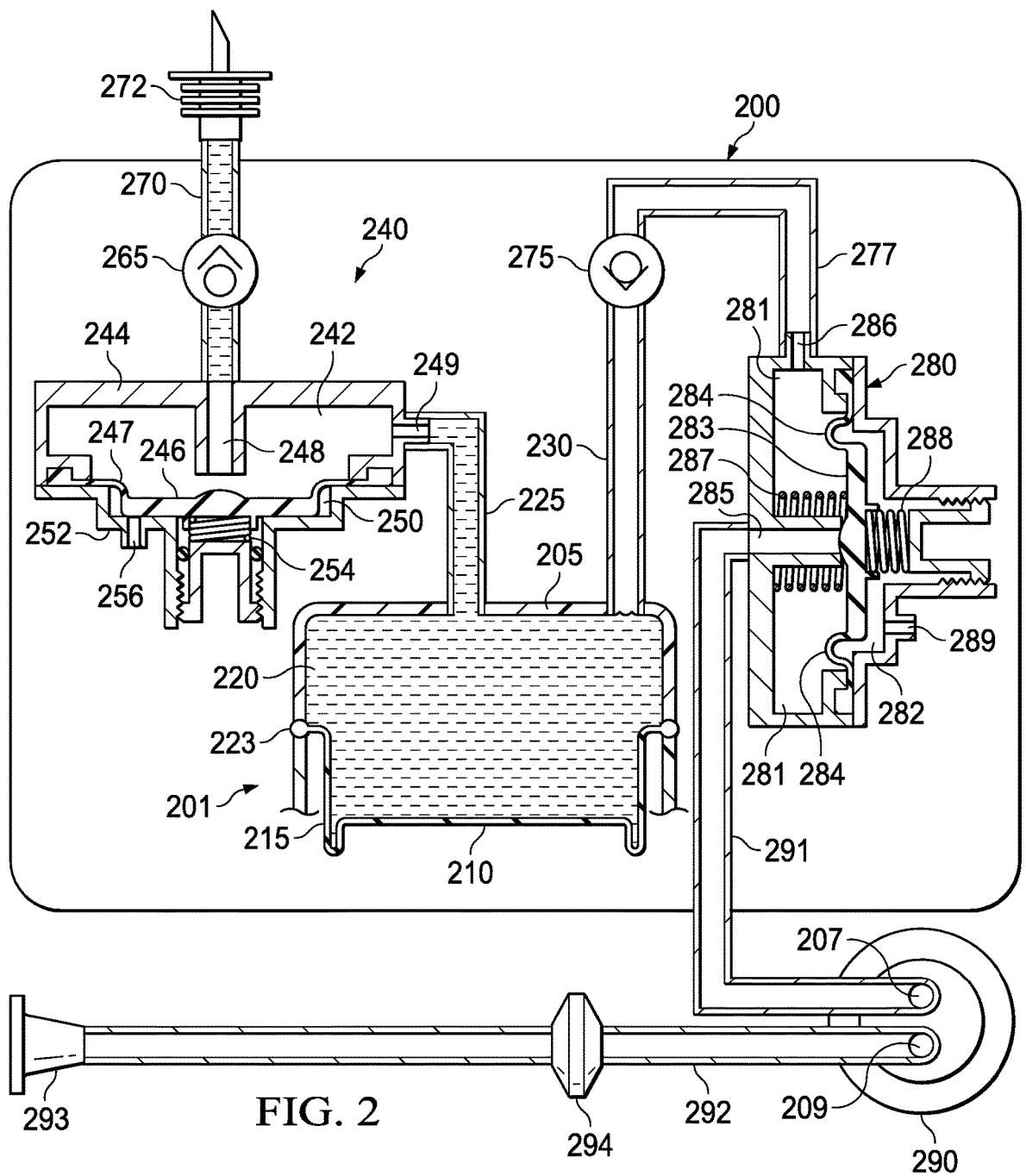
FIG. 2 is a schematic diagram illustrating additional details of a distribution system that may be associated with some example embodiments of the therapy system of FIG. 1, including some embodiments of an instillation pump including a dosing chamber.

FIG. 2 is a schematic diagram illustrating additional details of another example distribution system 200 that may be associated with some embodiments of the instillation pump 116. In the example embodiment of FIG. 2, the distribution system 200 may comprise a dosing valve 201 including a housing and a rolling diaphragm or other flexible barrier. For example, the dosing valve 201 may also comprise a dosing chamber substantially similar to dosing chamber 120 such as, for example, dosing chamber 220 defined by a housing 205 and a rolling diaphragm 210. In some embodiments, the housing 205 may be a half-cylinder, and is preferably sufficiently rigid to maintain its shape in operation. The rolling diaphragm 210 may comprise a flange 215, which can be coupled to the housing 205 to provide a seal across the housing 205, defining a pressure vessel having a variable volume and flexible, moving side-walls. The dosing chamber 220 may additionally comprise one or more fixation points 223, a dosing inlet 225, and a dosing outlet 230.

Figure 3A:
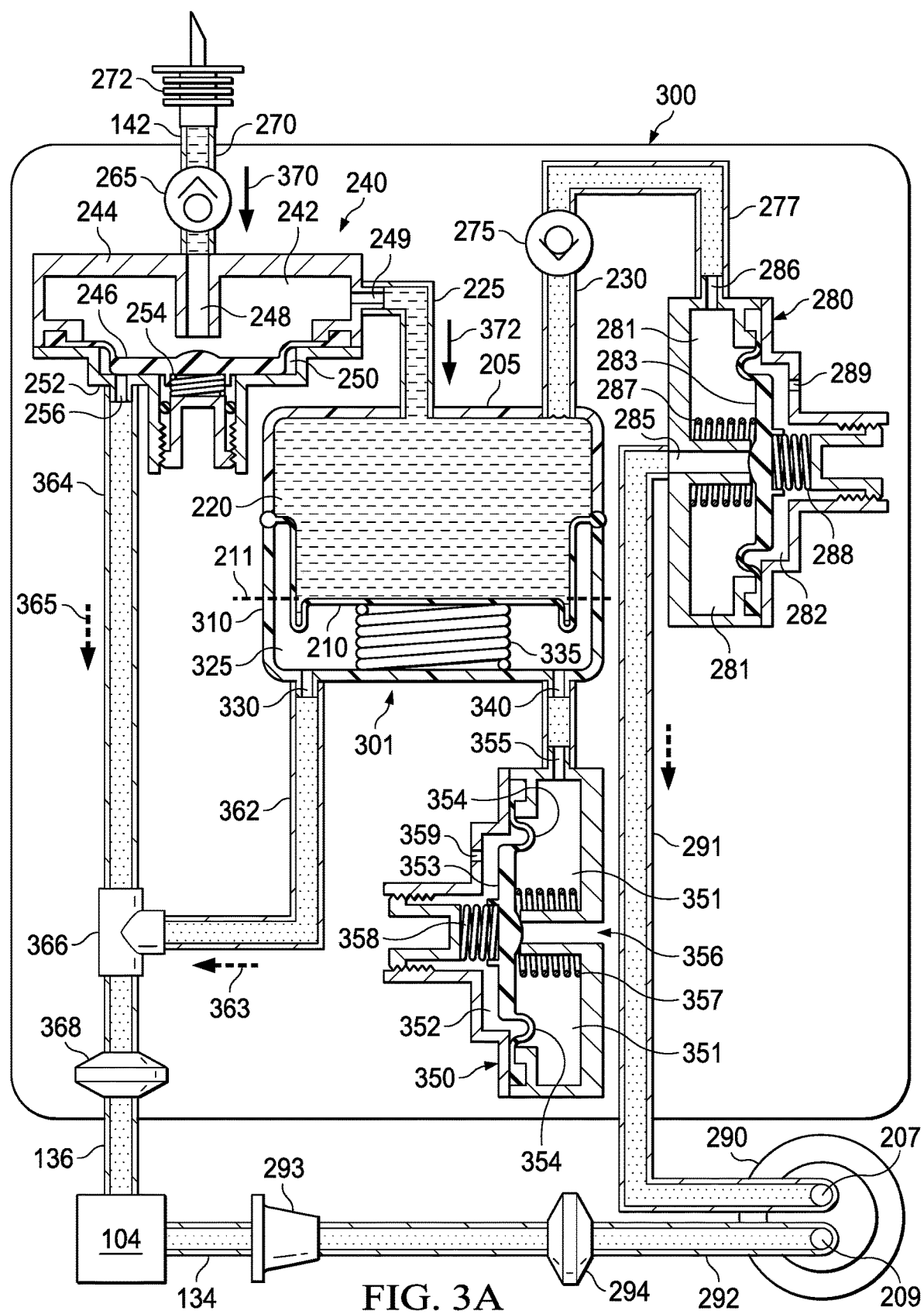
FIG. 3A is a schematic diagram illustrating additional details of a distribution system that may be associated with some example embodiments of the therapy system of FIG. 1, including some embodiments of an instillation pump being primed during a negative-pressure interval.
Figure 3B:
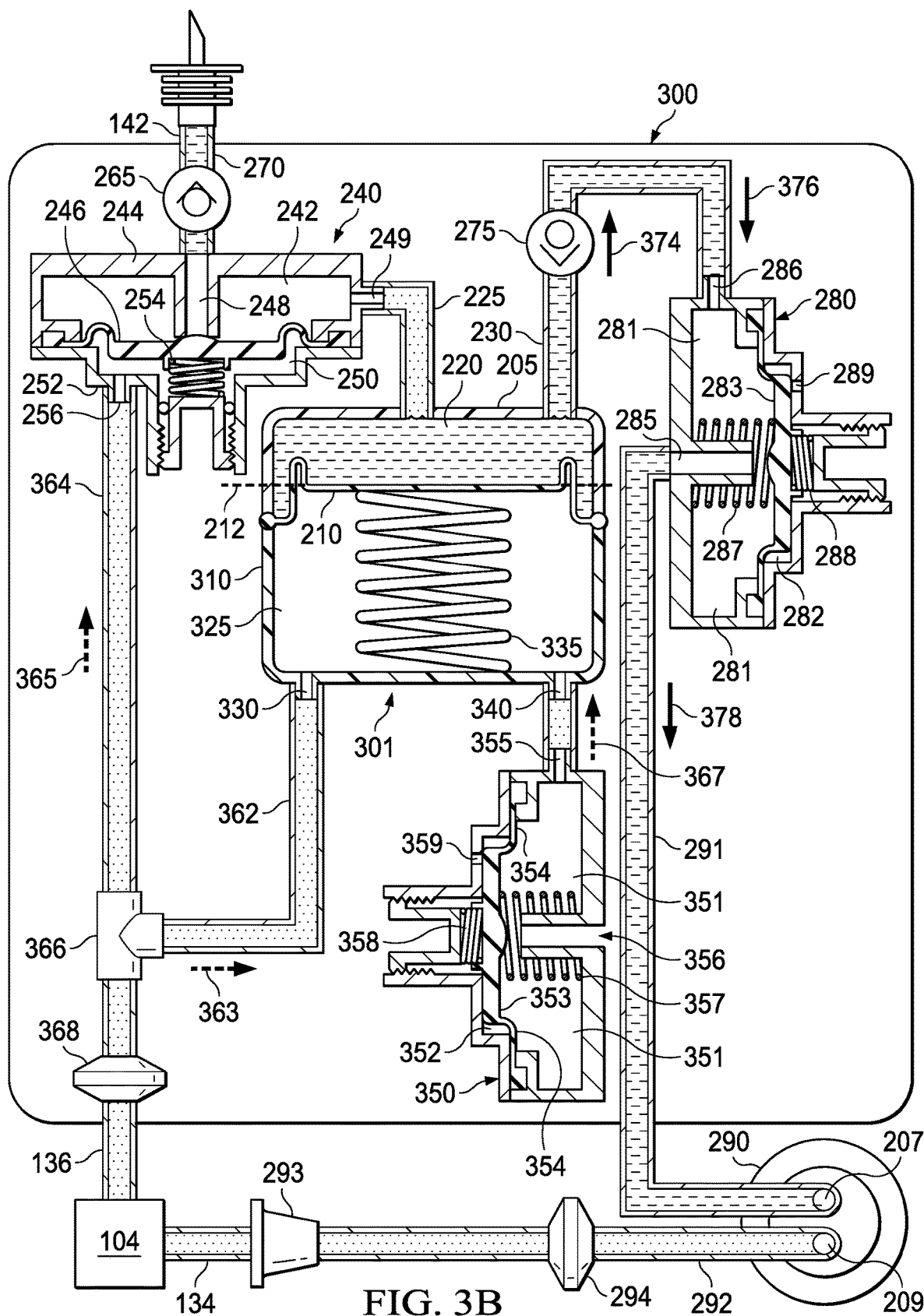
FIG. 3B is a schematic diagram illustrating additional details of a distribution system that may be associated with some example embodiments of the therapy system of FIG. 1, including some embodiments of an instillation pump instilling fluids during a venting interval.

As illustrated in FIG. 2, a valve may be fluidly coupled to the dosing inlet 225 such as, for example, priming valve 240. The priming valve 240 may comprise a priming chamber 242 that may include a housing 244 and a rolling diaphragm 246 or other flexible barrier. In some embodiments, the housing 244 may be a half-cylinder, and is preferably sufficiently rigid to maintain its shape in operation. The rolling diaphragm 246 may comprise a flange 247, which can be coupled to the housing 244 to provide a seal across the housing 244, defining a pressure vessel having a variable volume and flexible, moving side-walls. The priming chamber 242 may additionally comprise a fluid inlet 248 and a fluid outlet 249 that may be fluidly coupled to the dosing inlet 225 of the dosing chamber 220. The priming valve 240 may further comprise a working chamber 250 that may comprise a housing 252 and the rolling diaphragm 246, which divides the priming chamber 242 from the working chamber 250. The working chamber 250 may comprise a biasing element, such as a return spring 254 disposed between the housing 252 and the diaphragm 246. The return spring 254 can bias the diaphragm 246 away from the housing 252 toward the fluid inlet 248 in order to close the fluid inlet 248 so that the priming valve 240 is in a closed state, as shown in FIG. 3B. The working chamber 250 may also comprise a port, such as a fluid port 256 for receiving a negative pressure.

As further illustrated in FIG. 2, a first check valve 265 may be fluidly coupled to the fluid inlet 248 of the priming chamber 242. The check valve 265 may be any one of a duck-billed valve, a flap valve, a ball valve, a diaphragm valve, or a tilting disk valve. The first check valve 265 may be fluidly coupled to a first fluid conductor 270 that may be coupled to an interface 272 in some embodiments. The interface 272 may be configured to connect the first fluid conductor 270 to a solution source, such as the solution source 114. For example, in some embodiments, the interface 272 may be a connector configured to puncture a bag or port, such as a spike connector. In other embodiments, the first fluid conductor 270 may be directly coupled to the solution source 114.

The dosing outlet 230 of the dosing chamber 220 may be fluidly coupled to a second check valve 275, which may be fluidly coupled through a second fluid conductor 277 to a valve such as, for example, a control valve 280. The control valve 280 may comprise a housing enclosing a regulating chamber 281 and a working chamber 282 separated by a rolling diaphragm 283 or other flexible barrier. The rolling diaphragm 283 may comprise a flange 284, which can be coupled to the housing of the control valve 280 to provide a seal between the regulating chamber 281 and the working chamber 282. The regulating chamber 281 may additionally comprise a fluid outlet 285 and a fluid inlet 286 that may be fluidly coupled to the second fluid conductor 277. The regulating chamber 281 may additionally comprise a biasing element, such as a return spring 287 disposed between the diaphragm 283 and that portion of the housing enclosing the regulating chamber 281. The working chamber 282 may comprise a spring 288 disposed between the diaphragm 283 and that portion of the housing enclosing with the regulating chamber 281. The spring 288 can bias the diaphragm 283 toward the fluid outlet 285 in order to close the fluid outlet 285 to put the control valve 280 in a closed state as shown in FIGS. 2 and 3A. In some embodiments, the spring 288 may be used to calibrate operation of the return spring 287 to refine performance of the return spring 287 during the negative pressure and the venting intervals. The working chamber 282 may also comprise a port 289, which may be connected to an ambient environment for venting the working chamber 282.

The system 100 may comprise a fluid port 290 that is generally configured to fluidly couple various fluid conductors to various distribution components such as, for example, the dressing 102. The fluid port 290 is generally configured to fluidly couple the dressing 102 to other distribution components of the therapy system 100. The dressing 102 may include the cover 106 and the fluid port 290 in some embodiments. The fluid port 290 may comprise one fluid connector in some embodiments and more than one fluid connector in yet other embodiments. In some embodiments, for example, the fluid port 290 may comprise two fluid connectors including an installation connector 207 for providing instillation liquids to the dressing 102 and a negative pressure connector 209 for providing negative pressure to the dressing 102. For example, the system 100 may further comprise a third fluid conductor 291 having a first end fluidly coupled to the fluid outlet 285 of the control valve 280 and a second end fluidly coupled to the instillation connector 207 of the fluid port 290. The system 100 may further comprise a fourth fluid conductor 292 having a first end fluidly coupled to the negative pressure connector 209 of the fluid port 290 and a second end adapted to be fluidly coupled to a source of negative pressure such as, for example, the negative-pressure source 104. In some embodiments, the fourth fluid conductor 292 may be indirectly coupled to the negative pressure connector 209 by the third fluid conductor 291. In some embodiments, the third fluid conductor 291 may correspond to the fluid conductor 144 and the fourth fluid conductor 292 may correspond to the fluid conductor 132.

A fluid fitting 293 can be coupled to the other end of the fourth fluid conductor 292 opposite the fluid port 290. The fluid fitting 293 may be configured to fluidly couple the fourth fluid conductor 292 to an installation actuator, such as the instillation actuator 118 and ultimately to a source of negative pressure such as, for example, the negative-pressure source 104. In some embodiments, the fluid fitting 293 may be coupled directly to a source of negative pressure such as, for example, negative-pressure source 104. In other embodiments, the fluid fitting 293 may be coupled indirectly to a source of negative pressure through a container such as, for example, being coupled through the container 112 by the fluid conductors 132 and 134. A bacterial filter 294 may also be coupled to the fourth fluid conductor 292 between the fluid port 290 and the fluid fitting 293.

Referring now to FIG. 3A, a schematic diagram of an instillation pump 300 is shown illustrating additional details that may be associated with other example embodiments of the instillation pump 116 in conjunction with operation of the instillation pump 300 during a negative-pressure interval. FIG. 3B is a schematic diagram of the instillation pump 300 illustrating additional details that may be associated with other example embodiments of the instillation pump 116 in conjunction with operation of the instillation pump 300 during a venting interval. The instillation pump 300 shown in FIGS. 3A and 3B illustrate another example embodiment of the instillation actuator 118, including how the instillation actuator 118 may be coupled to the distribution system 200 of FIG. 2.

Figure 3C:
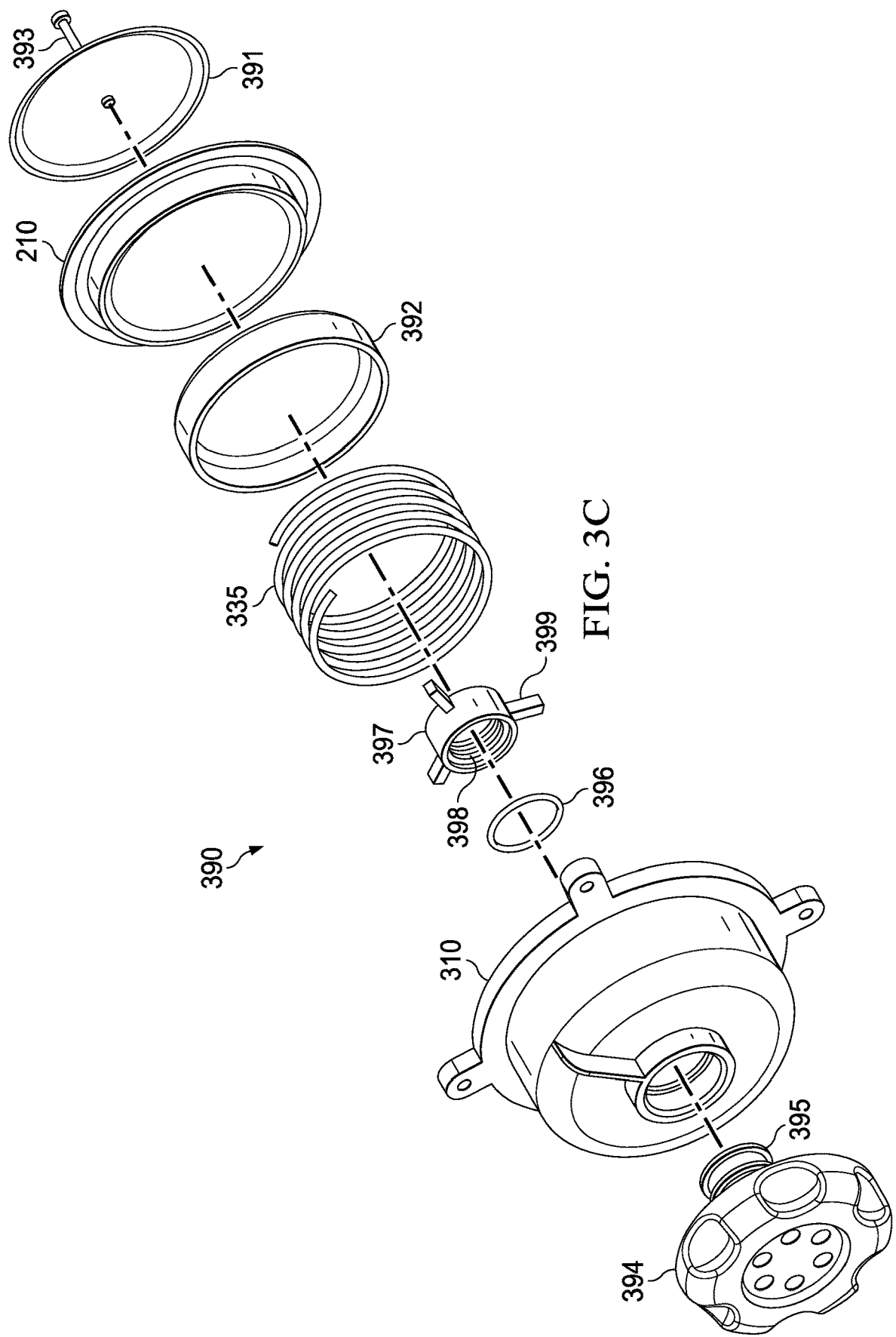
FIG. 3C is an exploded perspective schematic view of a rolling diaphragm subassembly that may be associated with some example embodiments of the instillation pump of FIGS. 3A and 3B.

The example embodiment of the instillation actuator 118 shown in FIGS. 3A and 3B may also comprise one or more pneumatic cylinders in some embodiments including a dosing valve 301. The dosing valve 301 in some embodiments of the instillation actuator 118 may comprise the dosing valve 201, a housing 310 that can be coupled to the housing 205 so that the housing 205 and the diaphragm 210 define a working chamber 325. The diaphragm 210 effectively partitions the dosing chamber 220 from the working chamber 325. In some embodiments, the instillation actuator 118 may additionally comprise a piston (not shown) operably engaged to the diaphragm 210, but the diaphragm 210 may effectively operate as a piston in some embodiments. For example, the diaphragm 210 may be sufficiently flexible to move under the influence of a pressure differential, or may be directly engaged to a biasing element such as, for example, a compression spring 335, as shown in FIGS. 3A, and 3B with more detail shown in FIG. 3C illustrating a rolling diaphragm subassembly 390 comprising the diaphragm 210 and the housing 310 that encloses the compression spring 335. The rolling diaphragm subassembly 390 does not show the fluid ports 330 and 340.

The rolling diaphragm subassembly 390 further comprises a support disk 391 disposed on an inner portion of the diaphragm 210 facing the dosing chamber 220 and a cylindrical piston 392 disposed on an inner portion of the other side of the diaphragm 210 disposed within the working chamber 325. The diaphragm 210 also comprises an outer portion fixed to the inside of the housing 310 to form the working chamber 325. The rolling diaphragm subassembly 390 further comprises an axle 393 having a first end fixed to the support disk 391 and a second end affixed to an adjustment dial 394 having a shaft 395 extending through the housing 310. In some embodiments, the shaft 395 may be rotationally coupled through a washer 396 to a compressor spindle 397 that engages the spring 335 within the working chamber 325. The compressor spindle 397 may comprise interior threads 398 for receiving the shaft 395 and outwardly extending spokes 399 for engaging the compression spring 335. The adjustment dial 394 may be rotated with respect to the compressor spindle 397 so that the compressor spindle 397 moves axially on the axle 393 against the compression spring 335 to increase or decrease the tension of spring 335 as the spring applies force against the piston 392 to move the diaphragm 312 in order to adjust the size of the dosing chamber 220.

A fluid port 330 may be fluidly coupled to the working chamber 325. A working fluid such as, for example, negative pressure may be provided to the working chamber 325 through the fluid port 330. For example, providing negative pressure to, or venting negative pressure from, the working chamber 325 can cause pressure changes in the working chamber 325. Providing negative pressure to the working chamber 325 may result in movement of the diaphragm 210 between a first position and a second position such as, for example, a first position 211 as shown in FIG. 3A and a second position 212 as shown in FIG. 3B. For example, providing negative pressure to the working chamber 325 may compress the compression spring 335 to the first position 211, while venting the negative pressure from the working chamber 325 may relax the compression spring 335 causing the diaphragm 210 to return to the second position 212. A fluid port 340 also may be fluidly coupled to the working chamber 325. In some embodiments, the fluid port 340 may be fluidly coupled to a valve such as, for example, a venting valve 350 for venting negative pressure from the working chamber 325 to provide ambient pressure. A working fluid entering the working chamber 325 through the fluid port 340 can reduce pressure in the working chamber 325 more quickly to accelerate movement of the diaphragm 210 between the first position 211 and the second position 212.

In some embodiments, the instillation actuator 118 may comprise a fifth fluid conductor, such as fifth fluid conductor 362 fluidly coupled to the working chamber 325 through the fluid port 330. In some embodiments, the fifth fluid conductor 362 may be fluidly coupled directly to a source of negative pressure, such as the negative-pressure source 104 through the fluid conductor 136. In some embodiments, the instillation actuator 118 may further comprise a sixth fluid conductor, such as sixth fluid conductor 364 fluidly coupled to the working chamber 250 through the fluid port 256 of the priming valve 240. In some embodiments, the sixth fluid conductor 364 may be fluidly coupled directly to a source of negative pressure, such as the negative-pressure source 104 through the fluid conductor 136. In some embodiments as shown, the fluid conductors 362 and 364 both may be coupled to the negative-pressure source 104 by a T-connector, such as fluid connector 366 which can be fluidly coupled directly to the negative-pressure source 104. A bacterial filter 368 can also be coupled to the fluid conductors 362 and 364 between the fluid ports 256 and 330 and the negative-pressure source 104 to prevent any fluids from flowing into the negative-pressure source 104.

The venting valve 350 may comprise a housing enclosing an ambient chamber 351 and a working chamber 352 separated by a rolling diaphragm 353 or other flexible barrier. The rolling diaphragm 353 may comprise a flange 354, which can be coupled to the housing of the venting valve 350 to provide a seal between the ambient chamber 351 and the working chamber 352. The ambient chamber 351 may additionally comprise a outlet port 355 fluidly coupled to the working chamber 352 and a fluid inlet 356 that may be fluidly coupled to the ambient environment to provide ambient pressure during the venting interval. The ambient chamber 351 may additionally comprise a biasing element, such as a return spring 357 disposed between the diaphragm 353 and a portion of the housing enclosing the ambient chamber 351. When negative pressure is provided to the ambient chamber 351, the diaphragm 210 10 compress the return spring 357 toward the fluid inlet 356 in order to close the fluid inlet 356 putting the venting valve 350 and a closed state as shown in FIG. 3A. The working chamber 352 also may comprise a spring 358 disposed between the diaphragm 353 and that portion of the housing enclosing the working chamber 352. The spring 358 can further bias the diaphragm 353 toward the fluid inlet 356 in order to close the fluid inlet 356 and put the venting valve 350 in the closed state. In some embodiments, the spring 358 may be used to calibrate operation of the return spring 357 to refine performance of the return spring 357 during the negative pressure and the venting intervals. The working chamber 352 may also comprise a port 359, that may be connected to an ambient environment for the venting the working chamber 352 in some embodiments.

As indicated above, FIG. 3A illustrates details that may be associated with example embodiments of the instillation pump 116, such as instillation pump 300, during a negative-pressure interval when negative pressure is being applied to the instillation pump 300, and FIG. 3B illustrates details that may be associated with example embodiments of the instillation pump 300, during a venting interval when negative pressure is not being applied. Referring more specifically to FIG. 4 in conjunction with FIGS. 3A and 3B, a graph illustrating additional details of some embodiments of the instillation pump 116, such as instillation pump 300, in operation and, more specifically, illustrating an example embodiment of a valve activation sequence during a negative-pressure interval when negative pressure is on and a venting interval when negative pressure is off.

Referring more specifically to FIGS. 4 and 3A, negative pressure may be applied to the fluid ports 256 and 330 of the working chamber 250 and the working chamber 325, respectively, to cause the priming chamber 242 of the priming valve 240 to fill and prime the dosing chamber 220 with instillation fluid drawn from a source of instillation fluid such as, for example, solution source 114. The valve actuation sequence includes the opening of the priming valve 240 and the check valve 265, along with the closing of the check valve 275, the priming valve 240, and control valve 280. For example, when negative pressure is applied to the fluid port 256 through the sixth fluid conductor 362, air flow as indicated by the dashed arrow 365 lowers the pressure within the working chamber 250. The lower pressure can cause the diaphragm 246 to overcome the resistance of the return spring 254 and compress the return spring 254 to open the priming valve 240. When the priming valve 240 opens, the instillation fluid begins flowing through the first fluid conductor 270 and the first check valve 265 into the priming chamber 242 as indicated by the solid arrow 370. The instillation fluid may then flow out of the priming chamber 242 through the fluid outlet 249 and the dosing inlet 225 to prime and begin filling the dosing chamber 220.

Negative pressure may also be applied to the fluid port 330 through the fifth fluid conductor 362 creating an air flow as indicated by the dashed arrow 363. The air flow lowers the pressure within the working chamber 325 causing the diaphragm 210 to overcome the resistance of the compression spring 335 and move to the first position 211 drawing the instillation fluid into the dosing chamber 220 until the dosing chamber 220 is filled with a predetermined volume of instillation fluid. When negative pressure is applied to motivate the diaphragm 210 to the first position 211, the check valve 275 closes to prevent any fluid from flowing back from the control valve 280 and the fluid port 290 through the second fluid conductor 277 and the third fluid conductor 291, respectively, into the dosing chamber 220.

In another example embodiment, negative pressure may be applied to the fluid outlet 285 of the control valve 280 through the third fluid conductor 291 creating airflow as indicated by the dashed arrow. The airflow may lower the pressure within the regulating chamber 281 so that the rolling diaphragm 283 overcomes the resistance of the return spring 287 to close the control valve 280. When the control valve 280 is closed, the control valve 280 may prevent any instillation fluid from flowing through the second fluid conductor 277 and the third fluid conductor 291 during the negative-pressure interval when the priming valve 240 begins priming the dosing chamber 220 with the instillation fluid. For example, when the controller 110 causes the negative-pressure source 104 to begin applying negative pressure as described above and shown in FIG. 4 at time zero, the control valve 280 may close at a time 401 prior to commencement of the priming valve 240 priming the dosing chamber 220 with the instillation fluid as described above.

In yet another example embodiment, negative pressure may be applied to the outlet port 355 of the venting valve 350 through the working chamber 325, the fluid port 330, and the fifth fluid conductor 362 creating airflow as indicated by the dashed arrow 363. The airflow may lower the pressure within the ambient chamber 351 so that the rolling diaphragm 353 overcomes the resistance of the return spring 357 to close the venting valve 350. When the venting valve 350 is closed, the venting valve 350 may allow the negative pressure within the working chamber 325 to increase more rapidly in order to reach a target pressure that is desired prior to allowing the priming valve 240 to begin priming the dosing chamber 220 with the instillation fluid. Reaching the target pressure more quickly may accelerate commencement of the priming operation as a result. For example, the venting valve 350 may be closed at a time 402 prior to commencement of the priming valve 240 priming the dosing chamber 220 with the instillation fluid so that the negative pressure within the working chamber 325 increases more rapidly from a pressure of about 75 mmHg to a desired target pressure of about 125 mmHg as shown at a time 403.

In some embodiments when the priming valve 240 draws instillation fluid from the solution source 114 into the dosing chamber 220 as described above, the return spring 254 of the priming valve 240 may be calibrated to ensure that the priming valve 240 is not opened too early in the negative pressure interval in order to avoid expelling instillation fluid from the dosing chamber 220 through the control valve 280 to the fluid port 290 prematurely. The return spring 254 of the priming valve 240 may also be calibrated to ensure that the priming valve 240 does open in a timely fashion so that the dosing chamber 220 is able to expel instillation fluid through the control valve 280 to the fluid port 290 in accordance with the prescribed therapy. For example, the return spring 254 may be calibrated so that the priming valve 240 does not open prior to the time when the control valve 280 and venting valve 350 close at the times 401 and 402, respectively, to prevent instillation fluid from flowing through the control valve 280 to the fluid port 290. In other example embodiments, the priming valve 240 may be calibrated to open when the negative pressure applied to the working chamber 250 reaches the target pressure, e.g., the lowest therapy pressure, but not before as a result of the fluid head height of priming valve 240 and the control valve 280 along with the dosing chamber 220. For example, the priming valve 240 may be calibrated to open when the negative pressure in the working chamber 250 reaches a pressure of about 130 mmHg to achieve a desired target pressure of about 125 mmHg as shown at a time 403 in order to overcome the fluid head height of all the components.

When the negative pressure being applied reaches the desired target pressure, e.g., about 125 mmHg, the priming valve 240 may open as described above to begin priming and filling the dosing chamber 220 at the time 403, and the dosing chamber 220 may continue to fill with instillation fluid until the dosing chamber 220 is filled with the predetermined volume of instillation fluid at a time 404. The time period during which negative pressure is being applied to the instillation pump 116 such as, for example, the instillation pump 300, such time period may be referred to as the negative pressure interval when negative pressure is turned on and increased to the target pressure as described above. In this example embodiment, the negative pressure is turned on and left on until the dosing chamber 220 is filled with the predetermined volume of instillation fluid. When the negative pressure is turned off and no longer being applied, the negative pressure begins decreasing at the time 404 until the pressure reaches atmospheric pressure at, for example, a time 407. The time period during which negative pressure being applied to the instillation pump 116 such as, for example, the instillation pump 300, is decreasing may be referred to as the venting interval as described above. In some embodiments, the instillation of fluids may continue for a period of time after the venting interval is completed as shown at a time 408.

Referring more specifically to FIGS. 4 and 3B, negative pressure may be turned off at time 204 so that the negative pressure begins to decrease towards ambient pressure to commence the venting interval as shown in FIG. 4. As venting begins, air can begin flowing through the fluid conductors 362 and 364 and the fluid ports 256 and 330 into the working chamber 250 and the working chamber 325, respectively, as indicated by the dashed arrows 363 and 365, respectively, causing the pressure in the working chamber 250 and the working chamber 325 to begin increasing towards ambient pressure. The increasing pressure, or decreasing negative pressure, can cause the priming chamber 242 of the priming valve 240 to stop filling the dosing chamber 220 with instillation fluid drawn from a source of instillation fluid such as, for example, solution source 114.

The valve actuation sequence for the venting interval includes the closing of the priming valve 240 and the check valve 265, along with the opening of the check valve 275, the priming valve 240 and the control valve 280. For example, when negative pressure begins decreasing causing air to flow into the working chamber 250 as indicated by the dashed arrow 365, the return spring 254 may begin to relax and force the diaphragm 246 toward the inlet 248 to close the priming valve 240. When the priming valve 240 closes, the first check valve 265 also closes and prevents any more instillation fluid from flowing through the first fluid conductor 270 and the first check valve 265 into the priming chamber 242. As a result, the instillation fluid may then be prevented from flowing out of the priming chamber 242 through the fluid outlet 249 and the dosing inlet 225 to stop filling the dosing chamber 220.

Negative pressure may also be reduced causing airflow through the fifth fluid conductor 362 and the fluid port 330 as indicated by the dashed arrow 363 in order to vent the negative pressure from the working chamber 325. As the pressure increases in the working chamber 325, or the negative pressure decreases, the compression spring 335 may begin to relax and force the diaphragm 210 toward the second position 212 in order to expel the predetermined volume of instillation fluid from the dosing chamber 220 through the dosing outlet 230 and the second fluid conductor 277. The second check valve 275 may open when the flow of instillation fluid reverses as indicated by a solid arrow 374 allowing the compression spring 335 to force the rolling diaphragm 210 toward the second position 212. The rolling diaphragm 210 can cause the instillation fluid to begin flowing from the dosing chamber 220 into the control valve 280 and, ultimately, to the fluid port 290 through the second fluid conductor 277 and the third fluid conductor 291, respectively.

In another example embodiment, negative pressure may be vented from the outlet port 355 of the venting valve 350 into the working chamber 325 causing air to flow into the working chamber 325 as indicated by a dashed arrow 367. As air begins flowing from the working chamber 251 into the working chamber 325, the return spring 357 of the venting valve 350 may begin relaxing and forcing the diaphragm 353 to move away from the inlet 356 to open the venting valve 350 so that the inlet 356 can vent ambient pressure into the working chamber 325. Air may also be flowing through the fifth fluid conductor 362 and the fluid port 330 into the working chamber 325 as indicated by the dashed arrow 363, but at a relatively slow rate dependent on the leaks in the system as described above. Thus, when the venting valve 350 opens, air flowing through the fluid port into the working chamber 325 can accelerate venting of the working chamber 325 by decreasing negative pressure more rapidly within.

In some embodiments, an instillation pressure may be desired for commencing instillation of fluid from the dosing chamber 220, and that instillation pressure may be less than the target pressure for priming the dosing chamber 220 with instillation fluid. For example, the target pressure may be about 125 mmHg while the instillation pressure may be about 50 mmHg in some embodiments as shown in FIG. 4. In some embodiments it may be desirable to reach the instillation pressure more quickly, so that the instillation operation may commence more quickly and at a faster rate. For example, the venting valve 350 may be opened at a time 405 after the dosing chamber 220 has been filled with the instillation fluid at the time 404 so that the negative pressure within the working chamber 325 vents more rapidly from a pressure of about 75 mmHg to a desired instillation pressure of about 50 mmHg at a time 406. The instillation operation may commence when the negative pressure reaches the desired instillation pressure and continue after the negative pressure within the working chamber 325 reaches ambient pressure such as, for example, at a time 407. For example, instillation may continue after negative pressure returns to ambient pressure at a time 408 when instillation is completed. The instillation solution may dwell at the tissue site after completion of the instillation cycle until the negative pressure is applied again in a subsequent negative-pressure interval.

In yet another example embodiment, the diaphragm 210 may expel instillation fluid out of the dosing chamber 220 into the regulating chamber 281 as described above. The force of the instillation fluid and the return spring 287 may cause the rolling diaphragm 283 to move away from the fluid outlet 285 to open the control valve 280. When the control valve 280 is open, control valve 280 allows the instillation fluid to flow through the second check valve 275 as indicated by solid arrow 374, the second fluid conductor 277 as indicated by solid arrow 376, and the third fluid conductor 291 to the fluid port 290 as indicated by solid arrow 378. For example, the control valve 280 may open after the dosing chamber 220 has been filled with a predetermined volume of instillation fluid at the time 404 when the negative pressure reaches the desired instillation pressure as described above such as, for example, about 50 mmHg at the time 406, to begin the instillation of fluid from the dosing chamber 220 to the fluid port 290. The instillation operation continue for a period of time extending beyond the time when the working chamber 325 reaches ambient pressure to a time when all the fluid in the dosing chamber 220 is instilled into the fluid port 290 such as, for example, at a time 408. The second check valve 275 may be normally closed, creating a closed system of the solution source 114 and the dosing chamber 120. Expansion of the dosing chamber 220 reduces the pressure in the dosing chamber 120 under such conditions, creating a pressure gradient between the solution source 114 and the dosing chamber 120 that can move instillation solution from the solution source 114 through the first check valve 265 into the dosing chamber 120.

The amount of fluid transferred from the solution source 114 to the dosing chamber 120 can be calibrated by modifying certain system parameters. For example, the spring constant of the compression spring 335 or the tension on the compression spring 335 may be modified to change the stroke length of the diaphragm 210 in some embodiments. In some embodiments, the tension on the compression spring 335 may be modified manually as described above with respect to the rolling diaphragm subassembly 390. The adjustment dial 394 may be rotated with respect to the compressor spindle 397 so that the compressor spindle 397 moves axially against the compression spring 335 to increase or decrease the tension of the compression spring 335 as the compression spring 335 applies force against the diaphragm 312 in order to adjust the size of the dosing chamber 220. In some embodiments, the tension on the compression spring 335 may be modified electrically using a sensor that provides feedback to a linear actuator rather than a manual actuator. Alternatively or additionally, the size of the dosing chamber 120 may be increased or decreased according to therapeutic needs.

The first check valve 265 may be normally closed, and contracting the dosing chamber 120 can increase the pressure in the dosing chamber under such conditions, creating a pressure gradient between the dosing chamber 120 and the fluid port 290 that can move instillation solution from the dosing chamber 120 through the second check valve 275 into the second fluid conductor 277 and the third fluid conductor 291. The first check valve 435 can prevent instillation solution from being returned to the solution source 114 as the pressure increases. In some embodiments, the instillation solution can be delivered to the dressing 102 through the fluid port 290.

Figure 5:
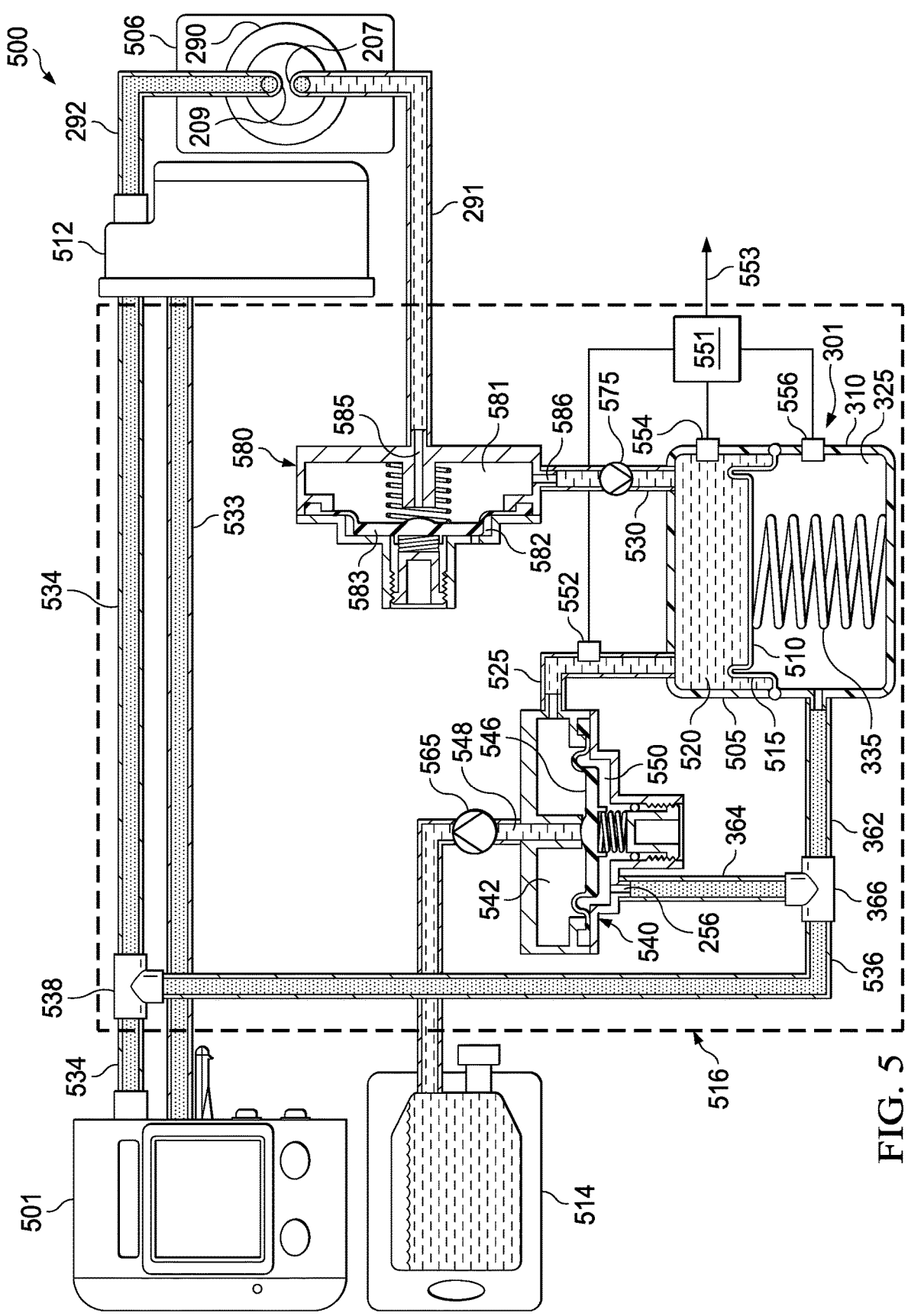
FIG. 5 is a schematic diagram of a second example embodiment of a therapy system that can provide negative-pressure and instillation in accordance with this specification.

Referring now to FIG. 5, a schematic diagram of an example embodiment of a second therapy system 500 is shown that can provide negative-pressure and instillation in accordance with this specification. In some embodiments of the therapy system 500, various components may correspond to those of FIGS. 1, 3A, and 3B and those components use reference numerals with similar digits. For example, the second therapy system 500 may comprise a negative pressure device 501, an instillation pump 516, a canister 512, and a solution source 514 fluidly coupled through a cover 506 to the tissue interface 108. These components may all be similar to the negative pressure device 101, the instillation pump 116, the container 112, and the solution source 114 fluidly coupled through the cover 106 to the tissue interface 108 as shown in FIG. 1. In some embodiments, the second therapy system 500 also may comprise fluid couplings 533, 534, and 536 that may be substantially similar to the fluid couplings 133, 134, and 136, respectively, of the first of therapy system 100. In a similar fashion, the second therapy system 500 also comprises components with a reference numbering scheme similar to the reference numbers of FIGS. 3A and 3B.

Referring more specifically to FIGS. 5 and 2 the instillation pump 516 may also comprise a dosing chamber substantially similar to dosing chamber 220 such as, for example, dosing chamber 520 comprising a housing 505 and a rolling diaphragm 510 are substantially similar to the housing 205 and the rolling diaphragm 210. In some embodiments, the housing 505 may be a half-cylinder, and is preferably sufficiently rigid to maintain its shape in operation. The rolling diaphragm 510 may comprise a flange 515, which may be coupled to the housing 505 to provide a seal across the housing 505, defining a pressure vessel having a variable volume and flexible, moving side-walls. The dosing chamber 520 may additionally comprise a dosing inlet 525 and a dosing outlet 530.

A valve may be fluidly coupled to the dosing inlet 525 such as, for example, priming valve 540. The priming valve 540 is substantially similar to the priming valve 240 described above in structure and operation and, as such, may comprise a priming chamber 542 defined by a housing and a rolling diaphragm 546 substantially similar to the priming chamber 242, the housing 244, and the rolling diaphragm 246. The priming valve 540 may further comprise a working chamber 550 formed by a housing and the rolling diaphragm substantially similar to the housing 252 and the rolling diaphragm 246, which divides the priming chamber 542 from the working chamber 550. The working chamber 550 may comprise a biasing element, such as a return spring substantially similar to the return spring 254, which biases the diaphragm 546 away from the housing 252 toward a fluid inlet 548, substantially similar to the fluid inlet 248, in order to close the fluid inlet 548. Closing the fluid inlet 548 causes the priming valve 540 to be placed a closed state, as shown in FIG. 3B. The working chamber 550 may also comprise a port substantially similar to the fluid port 256 for receiving a negative pressure. A first check valve 565 substantially similar to the first check valve 265 may be fluidly coupled to the fluid inlet 548 of the priming chamber 542. The first check valve 565 may be fluidly coupled to the solution source 514 through the first fluid conductor 270.

The dosing outlet 530 of the dosing chamber 520 may be fluidly coupled to a second check valve 575 substantially similar to the second check valve 275, which may be fluidly coupled through a second fluid conductor to a valve such as, for example, a control valve 580 substantially similar to the control valve 280 in structure and operation. The control valve 580 may comprise a housing enclosing a regulating chamber 581 and a working chamber 582 separated by a rolling diaphragm 583, all substantially similar to the corresponding components of the control valve 280 in structure and operation. The rolling diaphragm 583 may comprise a flange, which can be coupled to the housing of the control valve 580 to provide a seal between the regulating chamber 581 and the working chamber 582. The regulating chamber 581 may additionally comprise a fluid outlet 585 and a fluid inlet 586 that may be fluidly coupled to the second fluid conductor. The regulating chamber 581 may additionally comprise a biasing element, such as a return spring disposed between the diaphragm 583 and that portion of the housing enclosing the regulating chamber 581. The working chamber 582 may comprise a spring disposed between the diaphragm 583 and that portion of the housing enclosing the regulating chamber 581. The spring can bias the diaphragm 583 toward the fluid outlet 585 in order to close the fluid outlet 585 to put the control valve 580 in a closed state as shown in FIGS. 2 and 3A. In some embodiments, the spring may be used to calibrate operation of the return spring to refine performance of the return spring during the negative pressure and the venting intervals. The working chamber 582 may also comprise a port 589, which may be connected to an ambient environment for venting the working chamber 582.

The system 500 also may comprise the fluid port 290 that is generally configured to fluidly couple various fluid conductors to various distribution components such as, for example, the dressing 102. The fluid port 290 is generally configured to fluidly couple the dressing 102 to other distribution components of the therapy system 500. The dressing 102 may include the cover 506 and the fluid port 290 in some embodiments. The fluid port 290 may comprise one fluid connector in some embodiments and more than one fluid connector in yet other embodiments. In some embodiments, for example, the fluid port 290 may comprise two fluid connectors including an instillation connector 207 for providing instillation liquids to the dressing 102 and a negative pressure connector 209 for providing negative pressure to the dressing 102. For example, the system 500 may further comprise the third fluid conductor 291 having a first end fluidly coupled to the fluid outlet 585 of the control valve 580 and a second end fluidly coupled to the instillation connector 207 of the fluid port 290. The system 500 may further comprise a fourth fluid conductor 292 having a first end fluidly coupled to the negative pressure connector 209 of the fluid port 290 and a second end adapted to be fluidly coupled to a source of negative pressure such as, for example, the negative-pressure device 501 through the canister 512 and the fluid conductor 534. In some embodiments, the fourth fluid conductor 292 may be indirectly coupled to the negative pressure connector 209 by the third fluid conductor 291. In some embodiments, the third fluid conductor 291 may correspond to the fluid conductor 144 and the fourth fluid conductor 292 may correspond to the fluid conductor 132.

In some embodiments of the therapy system 500, the instillation pump 516 may comprise a venting valve (not shown) substantially similar to the venting valve 350 so that negative pressure may be vented from the working chamber 352 of the venting valve 350 into the working chamber 325 of the dosing valve 301 causing air to flow into the working chamber 325 as indicated by a dashed arrow 367 shown in FIG. 3B. When negative pressure is provided to the ambient chamber 351 as described above, the diaphragm 210 compresses the return spring 357 toward the fluid inlet 356 in order to close the fluid inlet 356 putting the venting valve 350 and a closed state as shown in FIG. 3A.

As indicated above, the negative pressure device 501 may further comprise other control and/or communication devices that may be associated with additional features of the controller 110. For example, the negative pressure device 501 may comprise a wireless transceiver (not shown) coupled to the controller 110 for communicating commands and data with other components of the therapy system 500. For example, the instillation pump 516 may comprise a wireless transceiver 551 coupled to various components of the instillation actuator 118 including, for example, the dosing valve 301, wherein the wireless transceiver 551 communicates with the wireless transceiver contained within the negative pressure device 501 as indicated by the arrow 553. In some embodiments, the wireless transceiver 551 may be coupled to pressure sensors coupled to various components of the dosing valve 301 to control the dosing and instillation process described above. For example, pressure sensors 552, 554, and 556 may be coupled directly or indirectly to the dosing input 525, the dosing chamber 520, and the working chamber 325, respectively, and electrically coupled to the wireless transceiver 551.

In some embodiments, the therapy system 500 is adapted to include only the negative pressure device 501 coupled directly to the canister 512 for providing negative pressure therapy to the dressing 102 through the fourth fluid conductor 292 and the negative pressure connector 209. In other embodiments, the negative pressure device 501, the canister 512, and the instillation pump 516 may be separate modules for providing negative pressure and/or instillation fluids to the dressing 102 from the negative pressure device 501 and the solution source 514. In some embodiments, the negative pressure device 501 may be directly coupled to the canister 512 or indirectly coupled to the canister 512 through the instillation pump 516. For example, the negative pressure device 501 may be directly coupled to the canister 512 to provide negative pressure to the dressing 102 via the fourth fluid conductor 292 and the negative pressure connector 209. The negative pressure device 501 may be adapted to be separated from the canister 512, so that the negative pressure device 501 may be coupled directly to the instillation pump 516 which is adapted to be coupled directly to the canister 512 to provide both negative pressure and instillation fluids the fluid port 290 through their respective fluid conductors and connectors as described above. Essentially, the negative pressure device 501, the canister 512, and the instillation pump 516 may be separate modules wherein the instillation pump 516 may be inserted between the negative pressure device 501 and canister 512 for providing instillation fluids through the third fluid conductor 291 and the fluid connector 207 to the dressing 102 as needed for providing instillation therapy or purging of the tissue site in conjunction with negative pressure therapy and drainage of fluids from the tissue site.

In some embodiments of the therapy system 500 that comprise separate modules, the fluid conductor 534 for providing negative pressure to the dressing 102 may be disposed within the instillation pump 516 and comprise a first end adapted to be releasably coupled to the canister 512 and a second end adapted to be releasably coupled to the negative pressure device 501. The fluid conductor 534 may also be fluidly coupled by a connector 538 to the fluid conductor 536 that provides negative pressure through the connector 366 to the working chamber 325 of the dosing valve 301 via the fluid conductor 362 and the working chamber 550 of the priming valve 540 via the fluid conductor 364. The operation of both the dosing valve 301 and the priming valve 540 in response to the application of negative pressure are both described in more detail above. In some embodiments of the therapy system 500, the instillation pump 516 may further comprise the fluid conductor 533 for measuring the negative pressure that may have a first end adapted to be releasably coupled to the canister 512 and a second end adapted to be releasably coupled to a pressure sensor such as, for example, the pressure sensor 122.

Figure 6A:
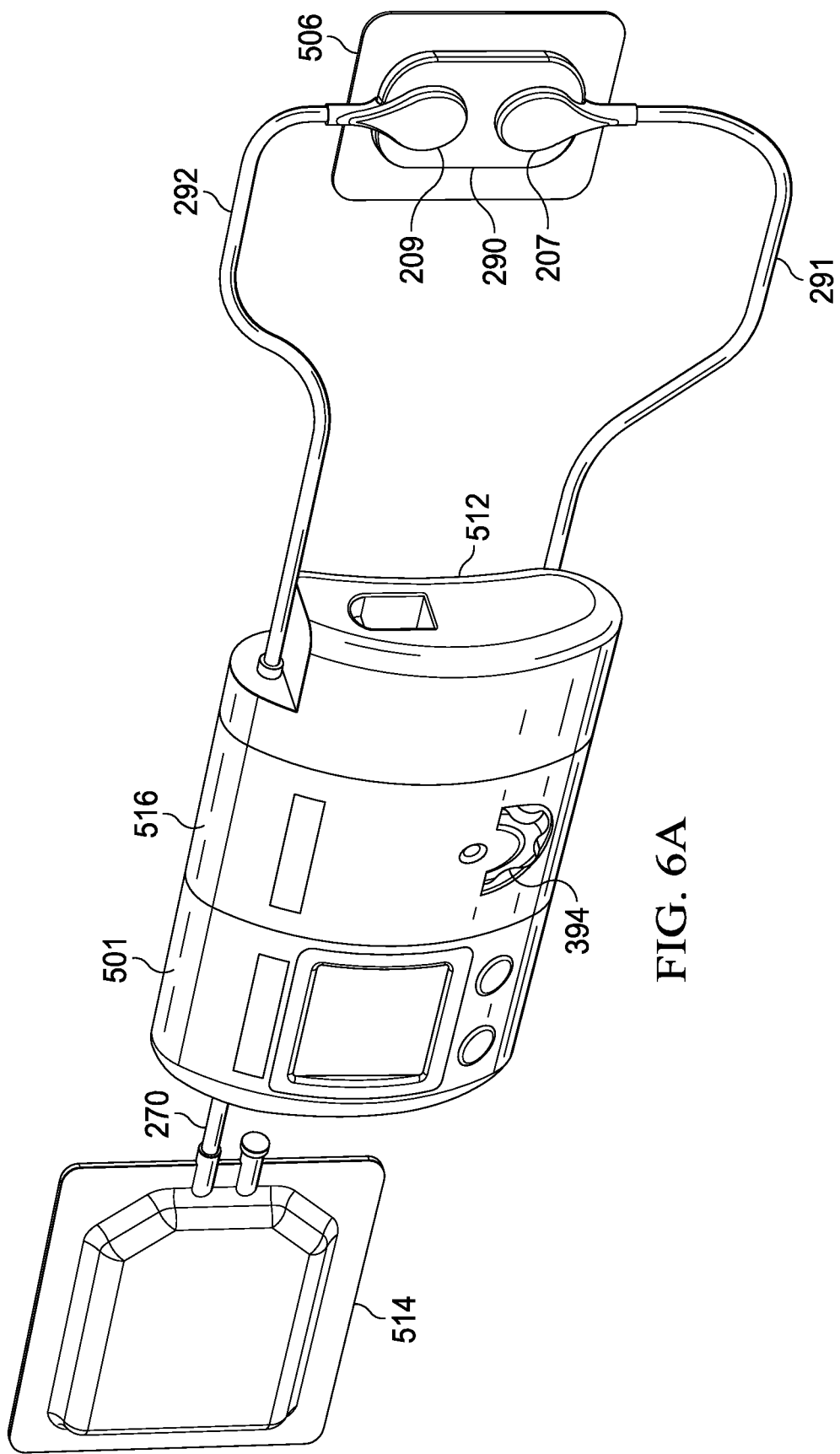
FIG. 6A is a perspective front view of a third example embodiment of a therapy system that can provide negative-pressure and instillation in accordance with this specification that may be associated with the therapy system of FIG. 5.
Figure 6B:
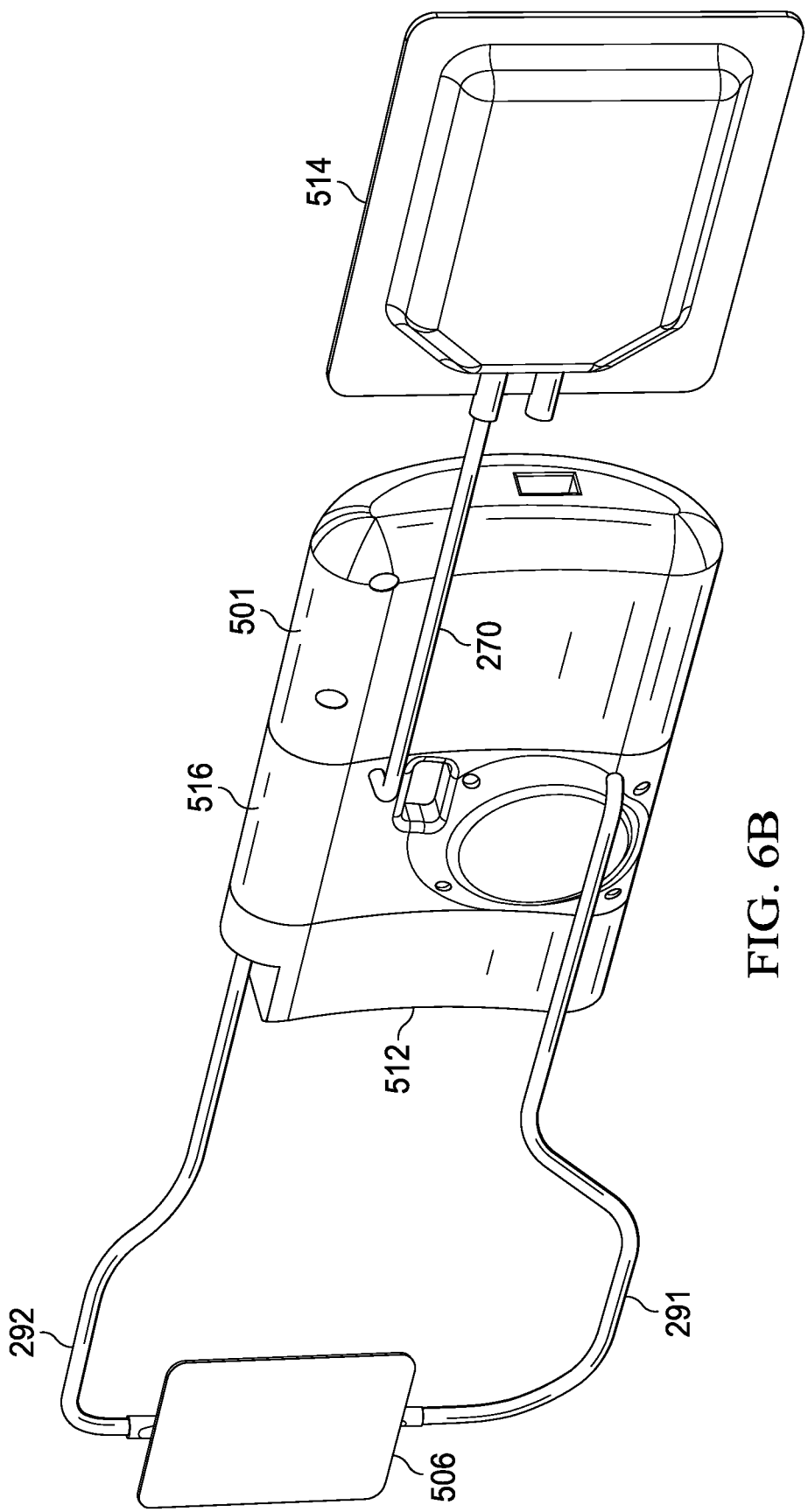
FIG. 6B is a perspective back view of the third example embodiment of a therapy system that can provide negative-pressure and instillation in accordance with this specification that may be associated with the therapy system of FIG. 5.

FIG. 6A is a perspective front view, and FIG. 6B is a perspective back view, of the therapy system 500 rather than a schematic view as shown in FIG. 5. In some embodiments of the therapy system 500 that comprise separate modules, the negative pressure device 501 may be adapted to be coupled directly to the instillation pump 516 which is adapted to be coupled directly to the canister 512 to provide both negative pressure and instillation fluids the fluid port 290 through their respective fluid conductors and connectors as described above. The negative pressure device 501, the canister 512, and the instillation pump 516 may function as separate modules, but also may be combined as a single unit wherein the instillation pump 516 may be inserted between the negative pressure device 501 and canister 512 for providing instillation fluids to the fluid port 290. More specifically, the instillation fluids from the solution source 514 through the first fluid conduit 270 and the instillation pump 516 to the fluid connector 207 through the third fluid conductor 291 and the fluid connector 207 as needed for providing instillation therapy to, or purging of, the dressing 102 in conjunction with negative pressure therapy and drainage of fluids from the dressing 102 and the tissue site from the negative pressure connector 209 through the fourth fluid conductor 292. Therapy systems such as therapy system 500 comprising separate modules that can accommodate a separate, modular instillation pump such as the instillation pump 516 can be much more cost-effective than two separate therapy systems, a first composite system comprising only a negative pressure device that interfaces with a canister for providing negative pressure therapy and a second composite system comprising integrated negative pressure and instillation components that interface with a canister for providing both negative pressure therapy and instillation when necessary.

As described above, FIG. 3A illustrates details that may be associated with example embodiments of the instillation pump 116, such as instillation pump 300, during a negative-pressure interval when negative pressure is being applied to the instillation pump 300, and FIG. 3B illustrates details that may be associated with example embodiments of the instillation pump 300, during a venting interval when negative pressure is not being applied. The instillation pump 516 described above operate in substantially the same way as described in conjunction with the graph shown in FIG. 4 illustrating additional details of some embodiments of the instillation pump 116, such as the instillation pump 516, in operation and, more specifically, illustrating an example embodiment of a valve activation sequence during a negative-pressure interval when negative pressure is on and a venting interval when negative pressure is off. In some embodiments, the negative-pressure device 501 may generate 125 mmHg (66 mbar) at the tissue site such that the instillation pump 516 may dose between 35 to 60 mL of fluid or solutions to the tissue site. In some embodiments, the instillation pump 516 may provide up to 12 instillation cycles per day with a median of 6 cycles per day. Thus, the negative pressure therapy treatments consume a vast majority of the time that the therapy system 500 operates under negative pressure. As indicated above, the instillation fluids may be a Saline solution, a Prontosan solution, or a Darkins instillation solution.

The systems, apparatuses, and methods described herein may provide significant advantages. For example, some therapy systems are known to provide intermittent negative-pressure therapy modes, and the instillation pump 116 can leverage such modes to deliver therapeutic fluids without substantially modifying the therapy system. The instillation pump 116 can also reduce the disposable footprint of the therapy system 100 while providing cost-effective delivery of therapeutic fluids to tissue sites. Much of the mechanical system, such as the instillation actuator 118, can be used by more than one patient. For example, the instillation pump 116 can provide a continuous fluid pathway that can be separated from a mechanical actuator, allowing another fluid pathway to be installed. Tubing, valves, fluid chambers, and associated components can be removed in some embodiments. The combined assembly can also provide all pressure seals and fitments to allow disposable elements to be installed and to maintain actuation pressure within a pressure chamber. The instillation pump 116 can be readily attached to a dressing and solution source, which can be a significant feature for patients and care providers outside of a medical facility.

The disposable elements can be combined with the mechanical elements in a variety of different ways to provide therapy. For example, in some embodiments, the disposable and mechanical systems can be combined inline, externally mounted, or internally mounted.

While shown in a few illustrative embodiments, a person having ordinary skill in the art will recognize that the systems, apparatuses, and methods described herein are susceptible to various changes and modifications. For example, certain features, elements, or aspects described in the context of one example embodiment may be omitted, substituted, or combined with features, elements, and aspects of other example embodiments. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An apparatus for managing fluids in a system for providing negative-pressure therapy to a tissue site, the apparatus comprising:
    a dosing chamber including a dosing inlet and a dosing outlet;
    a first check valve fluidly coupled to the dosing inlet and configured to be coupled to a source of liquids;
    a priming chamber fluidly coupled between the first check valve and the dosing inlet;
    a second check valve fluidly coupled to the dosing outlet;
    a first fluid conductor fluidly coupled to the second check valve;
    a fluid port fluidly coupled to the first fluid conductor;
    a second fluid conductor fluidly coupled to the fluid port;
    a fluid fitting fluidly coupled to the second fluid conductor and configured to be coupled to a negative-pressure source; and
    an instillation actuator fluidly coupled to the fluid fitting and the dosing chamber, the instillation actuator configured to expand the dosing chamber and open the priming chamber in a first state, and then to close the priming chamber and contract the dosing chamber in a second state.

2. The apparatus of claim 1, wherein the first fluid conductor further comprises a control valve.

3. The apparatus of claim 1, wherein the fluid port comprises a connector fluidly coupled to the first fluid conductor and configured to provide fluid to the tissue site.

4. The apparatus of claim 1, wherein the fluid port comprises a connector fluidly coupled to the fluid fitting and configured to remove fluid from the tissue site.

5. The apparatus of claim 1, wherein the fluid port comprises a first connector fluidly coupled to the first fluid conductor and configured to provide fluid to the tissue site and a second connector fluidly coupled to the fluid fitting and configured to remove fluid from the tissue site.

6. The apparatus of claim 1, wherein the dosing chamber is formed by a housing including the dosing inlet and the dosing outlet, and closed at one end by a diaphragm.

7. The apparatus of claim 6, wherein the diaphragm is a rolling diaphragm.

8. The apparatus of claim 1, where the instillation actuator further comprises:
    a first piston chamber fluidly coupled to the fluid fitting;
    a first piston operably engaged to the dosing chamber and configured to be actuated by pressure changes in the first piston chamber to expand and contract the dosing chamber;
    a second piston chamber fluidly coupled to the fluid fitting; and
    a second piston operably engaged to the priming chamber and configured to be actuated by pressure changes in the second piston chamber to open and close the priming chamber.

9. The apparatus of claim 8, wherein any one of the first piston or the second piston comprises a spring.

10. The apparatus of claim 8, wherein the instillation actuator further comprises:
    a third piston chamber having a working chamber and an ambient chamber wherein the ambient chamber is fluidly coupled to the first piston chamber; and
    a valve mechanism disposed within the third piston chamber to partition the working chamber and the ambient chamber, and configured to open and close the ambient chamber to vent the first piston chamber when activated.

11. The apparatus of claim 10, wherein valve mechanism comprises a diaphragm to partition the working chamber and the ambient chamber.

12. The apparatus of claim 1, wherein the apparatus further comprises a dosing valve, the dosing valve comprising:
    a housing and a piston reciprocably disposed in the housing;
    the piston partitions the housing into the dosing chamber and a second chamber;
    the dosing chamber is fluidly coupled to the dosing inlet and the dosing outlet; and
    the second chamber is fluidly coupled to the second fluid conductor through the fluid fitting.

13. The apparatus of claim 1, wherein the apparatus further comprises a priming valve, the priming valve comprising:
    a housing and a piston reciprocably disposed in the housing;
    the piston partitions the housing into the priming chamber and a second chamber;
    the priming chamber is fluidly coupled between the first check valve and the dosing inlet; and
    the second chamber is fluidly coupled to the second fluid conductor through the fluid fitting.

14. The apparatus of any one of claims 12 and 13, wherein the piston comprises a diaphragm.

15. The apparatus of claim 1, further comprising a source of instillation solution fluidly coupled to the first check valve.

16. The apparatus of claim 1, further comprising a negative-pressure source fluidly coupled to the fluid fitting.

17. The apparatus of claim 1, further comprising a negative-pressure source fluidly coupled to the fluid fitting, the negative-pressure source configured to draw instillation solution into the priming chamber and into the dosing chamber through the dosing inlet during a negative-pressure interval and to expel instillation solution from the dosing chamber through the dosing outlet to the fluid port during a venting interval.

18. The apparatus of claim 1, where the instillation actuator further comprises:
    a first working chamber fluidly coupled to the fluid fitting;
    a first piston operably engaged to the priming chamber and configured to be actuated by applying negative pressure to the first working chamber to open the priming chamber;
    a second working chamber fluidly coupled to the fluid fitting; and
    a second piston operably engaged to the dosing chamber and configured to be actuated by applying negative pressure to the second working chamber to expand the dosing chamber.

19. The apparatus of claim 1, where the instillation actuator further comprises:
    a first working chamber fluidly coupled to the fluid fitting;
    a first piston operably engaged to the priming chamber and configured to be actuated by venting negative pressure from the first working chamber to close the priming chamber;
    a second working chamber fluidly coupled to the fluid fitting; and a second piston operably engaged to the dosing chamber and configured to be actuated by venting negative pressure from the second working chamber to contract the dosing chamber.

20. A method for managing fluid in a system for negative-pressure and instillation therapy, the method comprising:
fluidly coupling the apparatus of claim 1 to a dressing;
applying the dressing to a tissue site;
applying negative pressure to the tissue site for a first interval in which instillation solution is drawn into the dosing chamber through the priming chamber; and
venting negative pressure from the tissue site for a second interval in which instillation solution is delivered from the dosing chamber to the tissue site.

* * * * *